US012582517B2

(12) United States Patent
Levi et al.

(10) Patent No.: US 12,582,517 B2
(45) Date of Patent: **\*Mar. 24, 2026**

(54) SEALING MEMBER FOR PROSTHETIC HEART VALVE

(71) Applicant: Edwards Lifesciences Corporation, Irvine, CA (US)

(72) Inventors: Tamir S. Levi, Zikhron Yaakov (IL); Ziv Yohanan, Kfar Hahoresh (IL); David Maimon, Atlit (IL)

(73) Assignee: Edwards Lifesciences Corporation, Irvine, CA (US)

( \* ) Notice: Subject to any disclaimer, the term of this patent is extended or adjusted under 35 U.S.C. 154(b) by 1237 days.

This patent is subject to a terminal disclaimer.

(21) Appl. No.: 17/229,189

(22) Filed: Apr. 13, 2021

(65) Prior Publication Data

US 2021/0228342 A1     Jul. 29, 2021

Related U.S. Application Data

(63) Continuation of application No. 16/114,518, filed on Aug. 28, 2018, now Pat. No. 10,973,629.

(Continued)

(51) Int. Cl.
    *A61F 2/24*          (2006.01)
(52) U.S. Cl.
    CPC .......... *A61F 2/2409* (2013.01); *A61F 2/2418* (2013.01); *A61F 2/243* (2013.01);
    (Continued)
(58) Field of Classification Search
    CPC ...... A61F 2/2409; A61F 2/2418; A61F 2/243; A61F 2220/0091; A61F 2230/0054;
    (Continued)

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| CN | 103705315 B | 10/2015 |
| DE | 0144167 C | 9/1903 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Jerrah Edwards
*Assistant Examiner* — Teresa M Dudden
(74) *Attorney, Agent, or Firm* — Klarquist Sparkman, LLP

(57) ABSTRACT

A prosthetic heart valve can include a frame, a valve component, a sealing member, and a retaining member. The frame can be radially compressible and expandable between a radially-compressed configuration and a radially-expanded configuration. The valve component can be disposed within and coupled to the frame and have a plurality of leaflets. The sealing member can have a plurality of ribs and a plurality of connectors. The ribs can be coupled to and extend radially outwardly from the frame when the frame is in the radially-expanded configuration. The connectors can be coupled to and extend radially between the frame and the ribs. The sealing member can be configured to reduce or prevent perivalvular leakage around the prosthetic heart valve. The retaining member can be coupled to the frame and the sealing member and can retain the sealing member at a desired spacing relative to the frame.

15 Claims, 6 Drawing Sheets

Related U.S. Application Data

(60) Provisional application No. 62/554,933, filed on Sep. 6, 2017.

(52) U.S. Cl.
CPC ................ *A61F 2220/0091* (2013.01); *A61F 2230/0054* (2013.01); *A61F 2250/006* (2013.01); *A61F 2250/0069* (2013.01); *A61L 2430/20* (2013.01)

(58) Field of Classification Search
CPC ....... A61F 2250/006; A61F 2250/0069; A61L 2460/20
See application file for complete search history.

(56) References Cited

U.S. PATENT DOCUMENTS

| | | | |
|---|---|---|---|
| 3,587,115 | A | 6/1971 | Shiley |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| RE30,912 | E | 4/1982 | Hancock |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,266,073 | A | 11/1993 | Wall |
| 5,282,847 | A | 2/1994 | Trescony et al. |
| 5,295,958 | A | 3/1994 | Shturman |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,792 | A | 5/1997 | Lentell |
| 5,639,274 | A | 6/1997 | Fischell et al. |
| 5,665,115 | A | 9/1997 | Cragg |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,957,949 | A | 9/1999 | Leonhardt et al. |
| 6,027,525 | A | 2/2000 | Suh et al. |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,299,637 | B1 | 10/2001 | Shaolian et al. |
| 6,302,906 | B1 | 10/2001 | Goicoechea et al. |
| 6,338,740 | B1 | 1/2002 | Carpentier |
| 6,350,277 | B1 | 2/2002 | Kocur |
| 6,352,547 | B1 | 3/2002 | Brown et al. |
| 6,425,916 | B1 | 7/2002 | Garrison et al. |
| 6,440,764 | B1 | 8/2002 | Focht et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,979 | B2 | 3/2003 | Constantz et al. |
| 6,569,196 | B1 | 5/2003 | Vesely |
| 6,582,462 | B1 | 6/2003 | Andersen et al. |
| 6,605,112 | B1 | 8/2003 | Moll et al. |
| 6,652,578 | B2 | 11/2003 | Bailey et al. |
| 6,689,123 | B2 | 2/2004 | Pinchasik |
| 6,716,244 | B2 | 4/2004 | Klaco |
| 6,730,118 | B2 | 5/2004 | Spenser et al. |
| 6,733,525 | B2 | 5/2004 | Yang et al. |
| 6,767,362 | B2 | 7/2004 | Schreck |
| 6,769,161 | B2 | 8/2004 | Brown et al. |
| 6,783,542 | B2 | 8/2004 | Eidenschink |
| 6,830,584 | B1 | 12/2004 | Seguin |
| 6,878,162 | B2 | 4/2005 | Bales et al. |
| 6,893,460 | B2 | 5/2005 | Spenser et al. |
| 6,908,481 | B2 | 6/2005 | Cribier |

(56) References Cited

U.S. PATENT DOCUMENTS

| | | | |
|---|---|---|---|
| 6,936,067 | B2 | 8/2005 | Buchanan |
| 7,018,406 | B2 | 3/2006 | Seguin et al. |
| 7,018,408 | B2 | 3/2006 | Bailey et al. |
| 7,096,554 | B2 | 8/2006 | Austin et al. |
| 7,225,518 | B2 | 6/2007 | Eidenschink et al. |
| 7,276,078 | B2 | 10/2007 | Spenser et al. |
| 7,276,084 | B2 | 10/2007 | Yang et al. |
| 7,316,710 | B1 | 1/2008 | Cheng et al. |
| 7,318,278 | B2 | 1/2008 | Zhang et al. |
| 7,374,571 | B2 | 5/2008 | Pease et al. |
| 7,393,360 | B2 | 7/2008 | Spenser et al. |
| 7,462,191 | B2 | 12/2008 | Spenser et al. |
| 7,510,575 | B2 | 3/2009 | Spenser et al. |
| 7,563,280 | B2 | 7/2009 | Anderson et al. |
| 7,585,321 | B2 | 9/2009 | Cribier |
| 7,618,446 | B2 | 11/2009 | Andersen et al. |
| 7,618,447 | B2 | 11/2009 | Case et al. |
| 7,655,034 | B2 | 2/2010 | Mitchell et al. |
| 7,785,366 | B2 | 8/2010 | Maurer et al. |
| 7,959,665 | B2 | 6/2011 | Pienknagura |
| 7,959,672 | B2 | 6/2011 | Salahieh et al. |
| 7,993,394 | B2 | 8/2011 | Hariton et al. |
| 8,029,556 | B2 | 10/2011 | Rowe |
| 8,075,611 | B2 | 12/2011 | Millwee et al. |
| 8,128,686 | B2 | 3/2012 | Paul, Jr. et al. |
| 8,167,932 | B2 | 5/2012 | Bourang et al. |
| 8,291,570 | B2 | 10/2012 | Eidenschink et al. |
| 8,348,998 | B2 | 1/2013 | Pintor et al. |
| 8,449,606 | B2 | 5/2013 | Eliasen et al. |
| 8,454,685 | B2 | 6/2013 | Hariton et al. |
| 8,652,203 | B2 | 2/2014 | Quadri et al. |
| 8,747,463 | B2 | 6/2014 | Fogarty et al. |
| 9,078,781 | B2 | 7/2015 | Ryan et al. |
| 9,655,722 | B2 * | 5/2017 | Morriss ............... A61F 2/2436 |
| 2001/0021872 | A1 | 9/2001 | Bailey et al. |
| 2002/0026094 | A1 | 2/2002 | Roth |
| 2002/0032481 | A1 | 3/2002 | Gabbay |
| 2002/0138135 | A1 | 9/2002 | Duerig et al. |
| 2002/0143390 | A1 | 10/2002 | Ishii |
| 2002/0173842 | A1 | 11/2002 | Buchanan |
| 2003/0014105 | A1 | 1/2003 | Cao |
| 2003/0050694 | A1 | 3/2003 | Yang et al. |
| 2003/0100939 | A1 | 5/2003 | Yodfat et al. |
| 2003/0158597 | A1 | 8/2003 | Quiachon et al. |
| 2003/0212454 | A1 | 11/2003 | Scott et al. |
| 2004/0024452 | A1 | 2/2004 | Kruse et al. |
| 2004/0039436 | A1 | 2/2004 | Spenser et al. |
| 2004/0078074 | A1 | 4/2004 | Anderson et al. |
| 2004/0186558 | A1 | 9/2004 | Pavcnik et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0010285 | A1 | 1/2005 | Lambrecht et al. |
| 2005/0075725 | A1 | 4/2005 | Rowe |
| 2005/0075728 | A1 | 4/2005 | Nguyen et al. |
| 2005/0096736 | A1 | 5/2005 | Osse et al. |
| 2005/0096738 | A1 | 5/2005 | Cali et al. |
| 2005/0188525 | A1 | 9/2005 | Weber et al. |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2006/0004469 | A1 | 1/2006 | Sokel |
| 2006/0025857 | A1 | 2/2006 | Bergheim et al. |
| 2006/0058872 | A1 | 3/2006 | Salahieh et al. |
| 2006/0074484 | A1 | 4/2006 | Huber |
| 2006/0108090 | A1 | 5/2006 | Ederer et al. |
| 2006/0149350 | A1 | 7/2006 | Patel et al. |
| 2006/0183383 | A1 | 8/2006 | Asmus et al. |
| 2006/0229719 | A1 | 10/2006 | Marquez et al. |
| 2006/0259136 | A1 | 11/2006 | Nguyen et al. |
| 2006/0259137 | A1 | 11/2006 | Artof et al. |
| 2006/0287717 | A1 | 12/2006 | Rowe et al. |
| 2007/0005131 | A1 | 1/2007 | Taylor |
| 2007/0010876 | A1 | 1/2007 | Salahieh et al. |
| 2007/0010877 | A1 | 1/2007 | Salahieh et al. |
| 2007/0112422 | A1 | 5/2007 | Dehdashtian |
| 2007/0162102 | A1 | 7/2007 | Ryan et al. |
| 2007/0203503 | A1 | 8/2007 | Salahieh et al. |
| 2007/0203575 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Von Segesser et al. |
| 2007/0233228 | A1 | 10/2007 | Eberhardt et al. |
| 2007/0260305 | A1 | 11/2007 | Drews et al. |
| 2007/0265700 | A1 | 11/2007 | Eliasen et al. |
| 2008/0021546 | A1 | 1/2008 | Patz et al. |
| 2008/0114442 | A1 | 5/2008 | Mitchell et al. |
| 2008/0125853 | A1 | 5/2008 | Bailey et al. |
| 2008/0154355 | A1 | 6/2008 | Benichou et al. |
| 2008/0183271 | A1 | 7/2008 | Frawley et al. |
| 2008/0208327 | A1 | 8/2008 | Rowe |
| 2008/0243245 | A1 | 10/2008 | Thambar et al. |
| 2008/0255660 | A1 | 10/2008 | Guyenot et al. |
| 2008/0275537 | A1 | 11/2008 | Limon |
| 2008/0294248 | A1 | 11/2008 | Yang et al. |
| 2009/0099653 | A1 | 4/2009 | Suri et al. |
| 2009/0118826 | A1 | 5/2009 | Khaghani |
| 2009/0125118 | A1 | 5/2009 | Gong |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0299452 | A1 | 12/2009 | Eidenschink et al. |
| 2009/0319037 | A1 | 12/2009 | Rowe et al. |
| 2010/0049313 | A1 | 2/2010 | Alon et al. |
| 2010/0082094 | A1 | 4/2010 | Quadri et al. |
| 2010/0168844 | A1 | 7/2010 | Toomes et al. |
| 2010/0185277 | A1 | 7/2010 | Braido et al. |
| 2010/0198347 | A1 | 8/2010 | Zakay et al. |
| 2010/0204781 | A1 | 8/2010 | Alkhatib |
| 2011/0004299 | A1 | 1/2011 | Essinger et al. |
| 2011/0015729 | A1 | 1/2011 | Jimenez et al. |
| 2011/0066224 | A1 | 3/2011 | White |
| 2011/0137397 | A1 | 6/2011 | Chau et al. |
| 2011/0218619 | A1 | 9/2011 | Benichou et al. |
| 2011/0319991 | A1 | 12/2011 | Hariton et al. |
| 2012/0089223 | A1 | 4/2012 | Nguyen et al. |
| 2012/0101571 | A1 | 4/2012 | Thambar et al. |
| 2012/0123529 | A1 | 5/2012 | Levi et al. |
| 2012/0259409 | A1 | 10/2012 | Nguyen et al. |
| 2013/0023985 | A1 | 1/2013 | Khairkhahan et al. |
| 2013/0046373 | A1 | 2/2013 | Cartledge et al. |
| 2013/0150956 | A1 | 6/2013 | Yohanan et al. |
| 2013/0166017 | A1 | 6/2013 | Cartledge et al. |
| 2013/0190857 | A1 | 7/2013 | Mitra et al. |
| 2013/0274873 | A1 | 10/2013 | Delaloye et al. |
| 2013/0304200 | A1 | 11/2013 | McLean et al. |
| 2013/0310926 | A1 | 11/2013 | Hariton |
| 2013/0317598 | A1 | 11/2013 | Rowe et al. |
| 2013/0331929 | A1 | 12/2013 | Mitra et al. |
| 2014/0194981 | A1 | 7/2014 | Menk et al. |
| 2014/0200661 | A1 | 7/2014 | Pintor et al. |
| 2014/0209238 | A1 | 7/2014 | Bonyuet et al. |
| 2014/0222136 | A1 | 8/2014 | Geist et al. |
| 2014/0236287 | A1 | 8/2014 | Clague et al. |
| 2014/0277417 | A1 | 9/2014 | Schraut et al. |
| 2014/0277419 | A1 | 9/2014 | Garde et al. |
| 2014/0277424 | A1 | 9/2014 | Oslund |
| 2014/0277563 | A1 | 9/2014 | White |
| 2014/0296962 | A1 | 10/2014 | Cartledge et al. |
| 2014/0330372 | A1 | 11/2014 | Weston et al. |
| 2014/0343670 | A1 | 11/2014 | Bakis et al. |
| 2014/0343671 | A1 | 11/2014 | Yohanan et al. |
| 2014/0350667 | A1 | 11/2014 | Braido et al. |
| 2015/0073545 | A1 | 3/2015 | Braido |
| 2015/0073546 | A1 | 3/2015 | Braido |
| 2015/0135506 | A1 | 5/2015 | White |
| 2015/0157455 | A1 | 6/2015 | Hoang et al. |
| 2016/0193045 | A1 * | 7/2016 | Pollak .................. A61F 2/2412 |
| | | | 623/2.11 |
| 2016/0361160 | A1 | 12/2016 | Braido et al. |
| 2017/0014229 | A1 | 1/2017 | Nguyen-Thien-Nhon et al. |
| 2017/0143485 | A1 | 5/2017 | Gorman, III et al. |

(56) References Cited

U.S. PATENT DOCUMENTS

| | | | |
|---|---|---|---|
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |

FOREIGN PATENT DOCUMENTS

| | | | |
|---|---|---|---|
| DE | 2246526 A1 | 3/1973 | |
| DE | 19532846 A1 | 3/1997 | |
| DE | 19546692 A1 | 6/1997 | |
| DE | 19857887 A1 | 7/2000 | |
| DE | 19907646 A1 | 8/2000 | |
| DE | 10049812 A1 | 4/2002 | |
| DE | 10049813 C1 | 4/2002 | |
| DE | 10049814 A1 | 4/2002 | |
| DE | 10049815 A1 | 4/2002 | |
| EP | 0103546 A1 | 3/1984 | |
| EP | 0850607 A1 | 7/1998 | |
| EP | 1057460 A1 | 12/2000 | |
| EP | 1088529 A2 | 4/2001 | |
| EP | 1570809 A1 | 9/2005 | |
| FR | 2788217 A1 | 7/2000 | |
| FR | 2815844 A1 | 5/2002 | |
| GB | 2056023 A | 3/1981 | |
| SU | 1271508 A1 | 11/1986 | |
| WO | 9117720 A1 | 11/1991 | |
| WO | 9217118 A1 | 10/1992 | |
| WO | 9301768 A1 | 2/1993 | |
| WO | 9724080 A1 | 7/1997 | |
| WO | 9829057 A1 | 7/1998 | |
| WO | 9930646 A1 | 6/1999 | |
| WO | 9933414 A1 | 7/1999 | |
| WO | 9940964 A1 | 8/1999 | |
| WO | 9947075 A1 | 9/1999 | |
| WO | 0018333 A1 | 4/2000 | |
| WO | 0041652 A1 | 7/2000 | |
| WO | 0135878 A2 | 5/2001 | |
| WO | 0149213 A2 | 7/2001 | |
| WO | 0154624 A1 | 8/2001 | |
| WO | 0154625 A1 | 8/2001 | |
| WO | 0162189 A1 | 8/2001 | |
| WO | WO-2001062189 A1 | 8/2001 | |
| WO | 0047139 A9 | 9/2001 | |
| WO | 0164137 A1 | 9/2001 | |
| WO | WO-2001064137 A1 | 9/2001 | |
| WO | 0176510 A2 | 10/2001 | |
| WO | 0222054 A1 | 3/2002 | |
| WO | 0236048 A1 | 5/2002 | |
| WO | 0241789 A2 | 5/2002 | |
| WO | 0243620 A1 | 6/2002 | |
| WO | 0247575 A2 | 6/2002 | |
| WO | 0249540 A2 | 6/2002 | |
| WO | 03047468 A1 | 6/2003 | |
| WO | 2005034812 A1 | 4/2005 | |
| WO | WO-2005055883 A1 | 6/2005 | |
| WO | 2005084595 A1 | 9/2005 | |
| WO | 2006005015 A2 | 1/2006 | |
| WO | 2006014233 A2 | 2/2006 | |
| WO | 2006032051 A2 | 3/2006 | |
| WO | 2006034008 A2 | 3/2006 | |
| WO | WO-2006111391 A1 | 10/2006 | |
| WO | 2006127089 A1 | 11/2006 | |
| WO | 2006138173 A2 | 12/2006 | |
| WO | 2005102015 A3 | 4/2007 | |
| WO | 2007047488 A2 | 4/2007 | |
| WO | WO-2007067942 A1 | 6/2007 | |
| WO | 2007097983 A2 | 8/2007 | |
| WO | WO-2008005405 A2 | 1/2008 | |
| WO | WO-2008015257 A2 | 2/2008 | |
| WO | 2008035337 A2 | 3/2008 | |
| WO | WO-2008091515 A2 | 7/2008 | |
| WO | 2008147964 A1 | 12/2008 | |
| WO | 2008150529 A1 | 12/2008 | |
| WO | WO-2009033469 A1 | 3/2009 | |
| WO | 2009042196 A2 | 4/2009 | |
| WO | 2009053497 A1 | 4/2009 | |
| WO | 2009061389 A2 | 5/2009 | |
| WO | 2009116041 A2 | 9/2009 | |
| WO | 2009149462 A2 | 12/2009 | |
| WO | 2010011699 A2 | 1/2010 | |
| WO | WO-2010121076 A2 | 10/2010 | |
| WO | 2013106585 A1 | 7/2013 | |
| WO | 2015085218 A1 | 6/2015 | |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Al-Khaja et al., "Eleven Years' Experience with Carpentier-Edwards Biological Valves in Relation to Survival and Complications", European Journal of Cardio-thoracic Surgery 3: pp. 305-311, 1989.

Andersen H.R., et al., "Transluminal Implantation of Artificial Heart Valves. Description of a New Expandable Aortic Valve and Initial Results with Implantation by Catheter Technique in Closed Chest Pigs," European Heart Journal, The European Society of Cardiology, Oxford University Press, United Kingdom, May 1, 1992, vol. 13, No. 5, pp. 704-708.

Andersen, H.R. "History of Percutaneous Aortic Valve Prosthesis," Herz No. 34. pp. 343-346. 2009.

Bailey S.R., "Percutaneous Expandable Prosthetic Valves," Textbook of Interventional Cardiology, 1994, vol. 2, 2nd Edition, pp. 1268-1276 (12 Pages).

Pavcnik D., et al., "Development and Initial Experimental Evaluation of a Prosthetic Aortic Valve for Transcatheter Placement," Cardiovascular Radiology, Apr. 1, 1992, vol. 183(1), pp. 151-154.

Ross, "Aortic Valve Surgery," Surgery of the Arotic Valves, Guy's Hospital, London, At a meeting of the Council on Aug. 4, 1966. pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Uchida et al., "Modifications of Gianturco Expandable Wire Stents", American Roentgen Ray Society, May 1988, pp. 1185-1187.

Wheatley D. J., "Valve Prostheses," Operative Surgery, 4th edition, 1986, pp. 415-424.

* cited by examiner

SEALING MEMBER FOR PROSTHETIC HEART VALVE

CROSS-REFERENCE TO RELATED APPLICATION

This application is a continuation of U.S. application Ser. No. 16/114,518, filed Aug. 28, 2018, now U.S. Pat. No. 10,973,629, which claims the benefit of U.S. Provisional Application No. 62/554,933, filed Sep. 6, 2017. The prior applications are incorporated by reference herein.

FIELD

The present disclosure relates to implantable, expandable prosthetic devices and to methods and apparatuses for such prosthetic devices.

BACKGROUND

The human heart can suffer from various valvular diseases. These valvular diseases can result in significant malfunctioning of the heart and ultimately require replacement of the native valve with an artificial valve. There are several known artificial valves and several known methods of implanting these artificial valves in humans. Because of the drawbacks associated with conventional open-heart surgery, percutaneous and minimally-invasive surgical approaches are garnering intense attention. In one technique, a prosthetic heart valve is configured to be implanted in a much less invasive procedure by way of catheterization. For example, collapsible transcatheter prosthetic heart valves can be compressed and percutaneously introduced in the compressed state with a delivery apparatus and expanded to a functional size at the desired position. A challenge in transcatheter prosthetic heart valves is control of perivalvular leakage around the valve, which can occur for a period of time following initial implantation.

SUMMARY

Disclosed herein are exemplary embodiments of prosthetic heart valves with sealing members. The sealing members can, for example, reduce and/or eliminate perivalvular leakage.

In one representative embodiment, a prosthetic heart valve can comprise a frame, a valve component, and a sealing member.

In some embodiments, the frame can have an inflow end portion, an outflow end portion, an intermediate portion disposed between the inflow and outflow end portions, and a plurality of struts. The frame can be radially compressible and expandable between a radially-compressed configuration and a radially-expanded configuration.

In some embodiments, the valve component can be disposed within and coupled to the frame and have a plurality of leaflets.

In some embodiments, the sealing member can have a plurality of ribs and a plurality of drapes. The ribs can be coupled to and extend radially outwardly from the frame when the frame is in the radially-expanded configuration. The drapes can be coupled to and extend radially between the frame and the ribs. The sealing member can be configured to reduce or prevent perivalvular leakage around the prosthetic heart valve.

In some embodiments, each of the ribs includes a first end portion connected to the inflow end portion of the frame and a second end portion connected to the intermediate portion of the frame.

In particular embodiments, the struts of the frame form rows of junctions where the struts are connected to each other, the first end portions of the ribs are connected to one row of junctions, and the second end portions of the ribs are connected to another row of junctions spaced from the one row of junctions.

In certain embodiments, the first end portion of each rib is circumferentially offset relative to the second end portion of the rib when the prosthetic heart valve is in the radially-expanded configuration.

In some embodiments, the first end portions of adjacent ribs are coupled to a first apex of the frame, and the second end portions of the adjacent ribs are coupled to a second apex of the frame.

In one particular embodiment, the ribs of the sealing member are coupled together in a zig-zag or undulating pattern extending circumferentially around the frame.

In some embodiments, the prosthetic heart valve further comprises a plurality of flexible cords connected to and extending between the frame and the ribs of the sealing member.

In certain embodiments, the cords are connected to the ribs at intermediate portions of the ribs disposed between the first and second end portions of the ribs.

In some embodiments, the prosthetic heart valve further comprises a skirt mounted on the frame, and the drapes have inner longitudinally-extending edges sutured to the skirt and outer longitudinally-extending edges secured to the ribs.

In particular embodiments, the drapes of the sealing member are first drapes, and the sealing member further comprises a plurality of second drapes that are coupled to the frame and the ribs and that are circumferentially disposed between adjacent ribs and the first drapes.

In some embodiments, the ribs and the drapes extend longitudinally along the frame.

In certain embodiments, the drapes comprise PET, PTFE, ePTFE, polyurethane, or polyester.

In some embodiments, the frame is at least partially self-expandable from the radially-compressed configuration to the radially-expanded configuration.

In certain embodiments, the frame is at least partially mechanically expandable from the radially-compressed configuration to the radially-expanded configuration.

In another representative embodiment, a prosthetic heart valve can comprise a frame, a valve component, and a sealing member. The sealing member can include a plurality of ribs, a plurality of first drapes, and a plurality of second drapes. The ribs can be coupled to and extend radially outwardly from the frame when the frame is in the radially-expanded configuration. The first drapes can be coupled to the frame and the ribs, be circumferentially aligned with the ribs, and radially extend between the frame and the ribs. The second drapes can be coupled to the frame, the ribs, and the first drapes.

In some embodiments, each of the first drapes is connected to a respective rib, and each of the second drapes extends circumferentially between adjacent ribs.

In particular embodiments, the ribs and the first drapes extend longitudinally along the frame.

In one embodiment, the first drapes extend from the frame in a first plane, and the second drapes extend from the frame in a second plane that is at least substantially perpendicular to the first plane.

In some embodiments, the prosthetic heart valve further comprises a plurality of flexible cords that are coupled to and extend between the frame and the ribs, and the second drapes are mounted to the cords.

In yet another representative embodiment, a prosthetic heart valve can comprise a frame, a valve component, and a sealing member. The sealing member can include a plurality of ribs, a plurality of drapes, and one or more cords. The ribs can be coupled to and extend radially outwardly from the frame when the frame is in the radially-expanded configuration. The drapes can be coupled to and extend radially between the frame and the ribs. The cords can be coupled to the frame and the ribs so as to limit radial expansion of the ribs relative to the frame. The sealing member can be configured to reduce or prevent perivalvular leakage around the prosthetic heart valve.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from other portions of this disclosure, including the detailed description, drawings, claims, and abstract.

DETAILED DESCRIPTION

General Considerations

Figure 1:
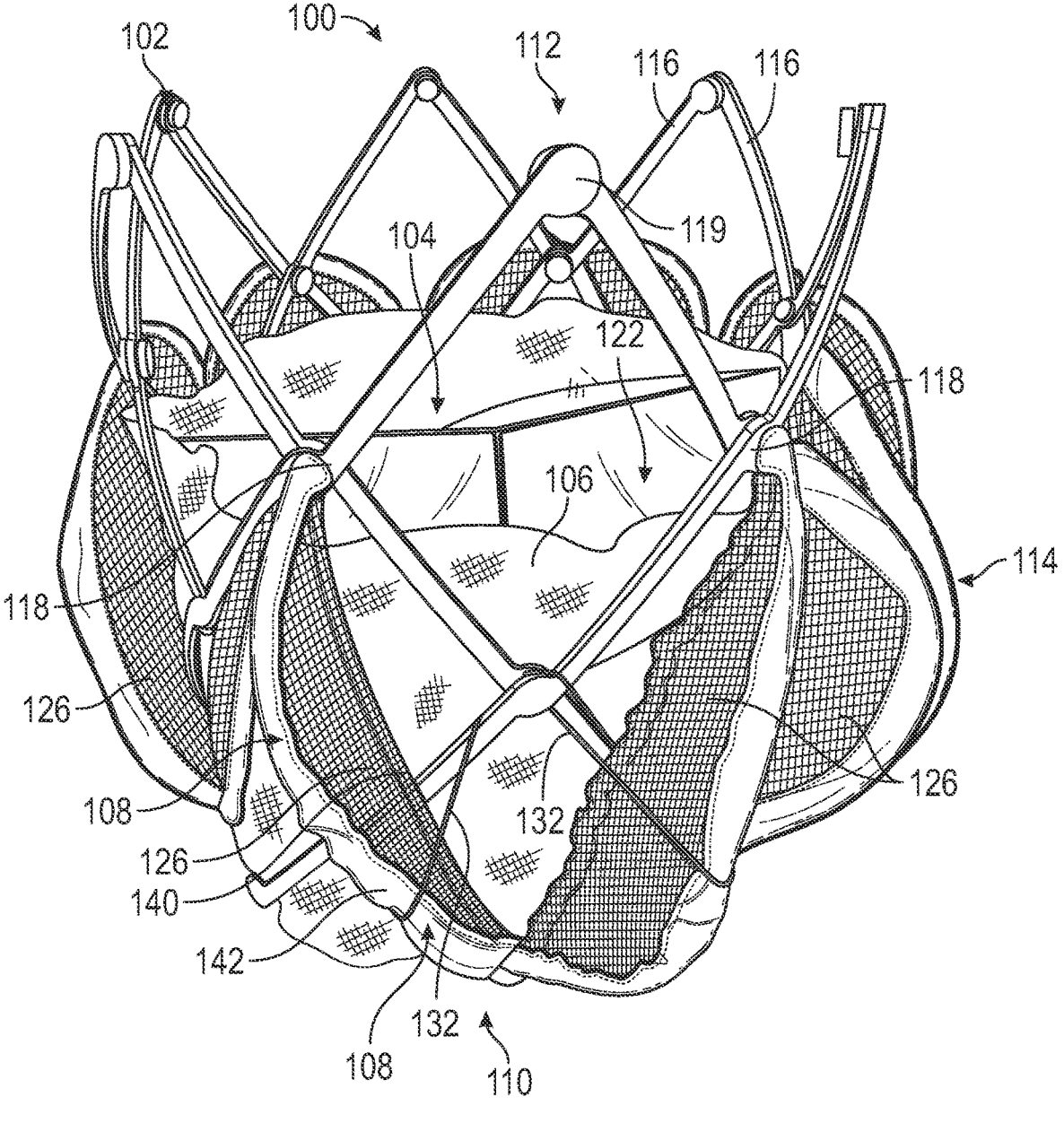
FIG. 1 depicts a prosthetic heart valve with a sealing member, according to one embodiment.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

As used herein, the term "approximately" means the listed value and any value that is within 10% of the listed value. For example, "approximately 100 degrees" means any angle between 90-110 degrees, inclusive.

EXEMPLARY EMBODIMENTS

Disclosed herein are exemplary embodiments of prosthetic heart valves with sealing members. The sealing members can, for example, reduce and/or eliminate perivalvular leakage ("PVL").

In some embodiments, a sealing member can comprise one or more ribs that extend radially outwardly from a frame of the prosthetic heart valve. In certain embodiments, the sealing member further comprises one or more drapes extending radially between the ribs and the frame.

In particular embodiments, the ribs and/or the drapes are flexible such the sealing member can conform to the anatomy of a native heart valve annulus. In this manner, the sealing member can reduce and/or eliminate PVL between a prosthetic heart valve and the native annulus.

In some embodiments, a sealing member can include a plurality of cords that are coupled to the ribs and the frame of the prosthetic heart valve. The cords can, for example, retain the position of the ribs relative to the frame.

In some embodiments, a sealing member can comprise first and second drapes. The first drapes can extend radially between the ribs and the frame of the prosthetic heart valve.

The second drapes can be coupled to and extend radially outwardly from the frame and can extend circumferentially between the first drapes.

FIGS. 1-6 show an exemplary embodiment of a prosthetic heart valve 100 and its components. Referring to FIG. 1, the prosthetic heart valve 100 can have four main components: a stent or frame 102, a valve structure 104, a skirt 106, and a perivalvular sealing means or sealing member 108. The frame 102 can be annular and can be configured to support the other components of the prosthetic heart valve 100. The valve structure 104 can be coupled to and disposed at least partially within the frame 102 and can be configured to regulate blood flow in one direction through the prosthetic heart valve 100. The skirt 106 can be coupled to the frame 102 and can be disposed on a radially-inwardly facing surface (as shown) and/or a radially-outwardly facing surface of the frame 102. The skirt 106 can be configured to reduce and/or prevent blood from flowing around the valve structure 104 and through the frame 102. The sealing member 108 can be coupled to and extend radially outwardly from the frame and/or the skirt 106. The sealing member 108 can be configured to reduce and/or eliminate PVL around the valve. Additional details of these components are provided below.

Figure 2:
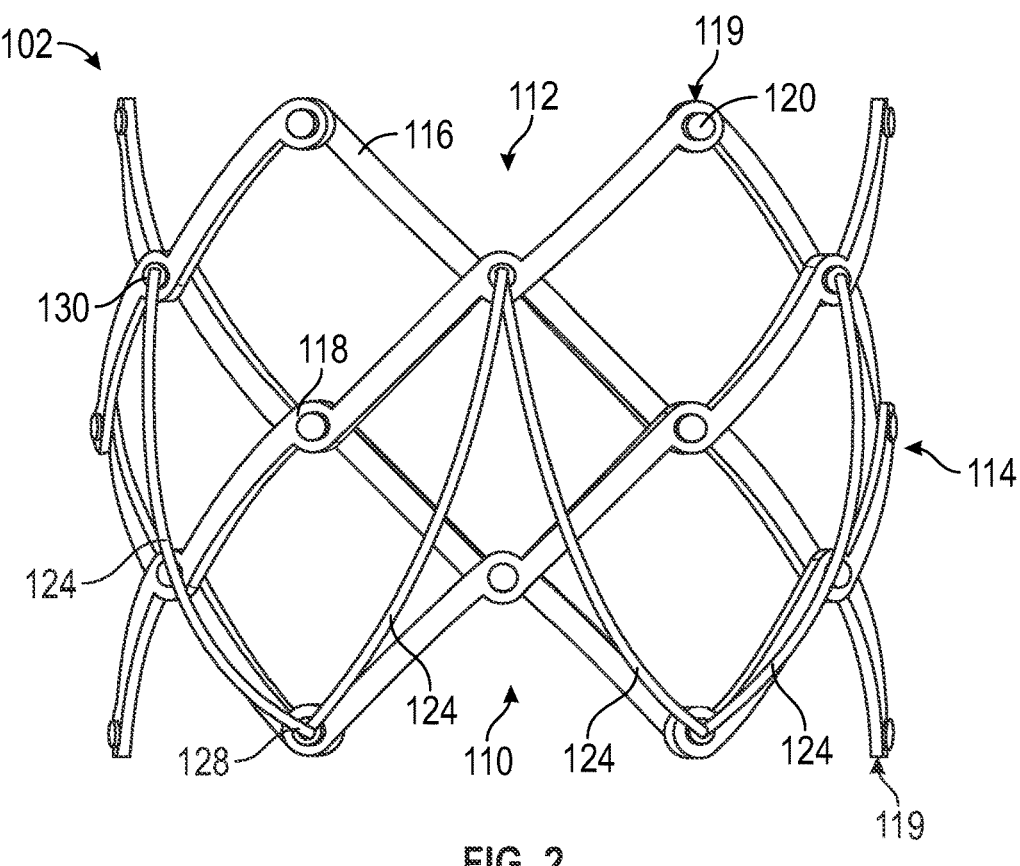
FIG. 2 depicts a frame and the sealing member (only partially shown) of the prosthetic heart valve of FIG. 1 in a radially-expanded configuration.

Referring to FIG. 2, the frame 102 can have an inflow end portion 110, an outflow end portion 112, and an intermediate portion 114 disposed between the inflow and outflow end portions 110, 112. The prosthetic heart valve 100 can define a longitudinal axis extending through the inflow end portion 110 and the outflow end portion 112.

The frame 102 can include a plurality of interconnected struts 116 arranged in a lattice-type pattern. The struts 116 can form a plurality of junctions 118 where the struts 116 intersect. The junctions 118 of the struts 116 disposed at the inflow and outflow end portions 110, 112 of the frame 102 can also be referred to as apices 119. The struts 116 are shown as positioned diagonally, or offset at an angle relative to, and radially offset from, the longitudinal axis of the prosthetic heart valve 100. In other embodiments and/or configurations, the struts 116 can be offset to a greater and/or lesser extent than depicted in FIG. 2, or some or all of the struts 116 can be positioned parallel to the longitudinal axis of the prosthetic heart valve 100 (see, e.g., FIG. 3).

In some embodiments, the struts 116 can be pivotably coupled to one another. In the illustrated embodiment, for example, the struts 116 form respective hinges at the junctions 118. In certain embodiments, fasteners (e.g., rivets or pins) 120 can be used to pivotably couple the struts 116 together. The hinges can allow the struts 116 to pivot relative to one another as the frame 102 is expanded or contracted, such as during assembly, preparation, and/or implantation of the prosthetic heart valve 100. For example, the frame 102 (and thus the prosthetic heart valve 100) can be manipulated into a radially-compressed or contracted configuration (e.g., FIG. 3) and inserted into a patient for implantation. Once inside the patient's body, the prosthetic heart valve 100 can be manipulated into an expanded state (e.g., FIGS. 1-2), as further described below.

The frame 102 can be formed using any suitable technique. Suitable techniques can include separately forming individual components (e.g., the struts 116 and fasteners 120) of the frame 102 and then mechanically assembling and connecting the individual components to form the frame 102. The struts 116 and fasteners 120 can be formed, for example, by laser cutting those components from sheets or tubes of metal, or by electroforming (electroplating or electrodeposition) or physical vapor deposition. In some embodiments, electroforming or physical vapor deposition can be used to form subcomponents of the frame 102 or the entire frame 102 with pivotable connections between the struts 116. In one embodiment, for example, electroforming or physical vapor deposition can be used to form struts 116 having integral fasteners 120. The individual struts 116 can be assembled together into a frame by inserting the integral fasteners 120 of each strut through a corresponding aperture of an adjacent strut. In some embodiments, electroforming or physical vapor deposition can be used to form the entire frame 102 in its final, cylindrical shape. In other embodiments, electroforming or physical vapor deposition can be used to form the entire frame in a flattened configuration, after which the ends of the flattened frame are connected to each other to form the final cylindrical shape of the frame.

In other embodiments, the struts 116 are not coupled to each other with respective hinges (e.g., fasteners) but are otherwise pivotable or bendable relative to each other to permit radial expansion and contraction of the frame. For example, the frame 102 can be formed (e.g., via laser cutting, electroforming or physical vapor deposition) from a single piece of material (e.g., a metal tube).

The frame 102 can be made of any of various suitable materials, such as stainless steel or a nickel titanium alloy ("NiTi"), for example, nitinol.

Additional details regarding the frame 102 can be found, for example, in U.S. Application No. 62/430,810, filed Dec. 6, 2016, and U.S. Patent Application Publication No. 2018/0153689, which are incorporated by reference herein.

Returning to FIG. 1, the valve structure 104 can regulate the flow of blood through the prosthetic heart valve 100. The valve structure 104 can comprise, for example, a leaflet assembly 122 comprising one or more leaflets made of a flexible material. The leaflets of the leaflet assembly 122 can be made from in whole or part, biological material (e.g., pericardial tissue, such as bovine, porcine, or equine pericardium), bio-compatible synthetic materials, and/or other such materials, including those described in U.S. Pat. No. 6,730,118, which is incorporated by reference herein. Further details regarding transcatheter prosthetic heart valves, including the manner in which the valve structure 104 can be coupled to the frame 102 of the prosthetic heart valve 100, can be found, for example, in U.S. Pat. Nos. 7,393,360, 7,510,575, 7,993,394, and 8,652,202, which are incorporated by reference herein.

As mentioned above, the skirt 106 can be mounted on the inside and/or outside of the frame 102. The skirt can be formed from natural tissue (e.g., pericardial tissue) or any of various biocompatible synthetic materials, including bio-compatible fabrics (e.g., polyethylene terephthalate ("PET") fabric). Additional details regarding the skirt 106, as well as the valve structure 104, can be found, for example, in U.S. Pat. No. 9,974,650, which is incorporated by reference herein.

The sealing member 108 can form a flexible structure that extends radially outwardly from the frame 102 of the prosthetic heart valve 100 when the prosthetic heart valve is in the radially-expanded configuration. As such, the sealing member 108 can, for example, conform to the anatomy of a native annulus and restrict or block blood flow around the prosthetic heart valve 100, thereby eliminating or reducing PVL.

Figure 4:
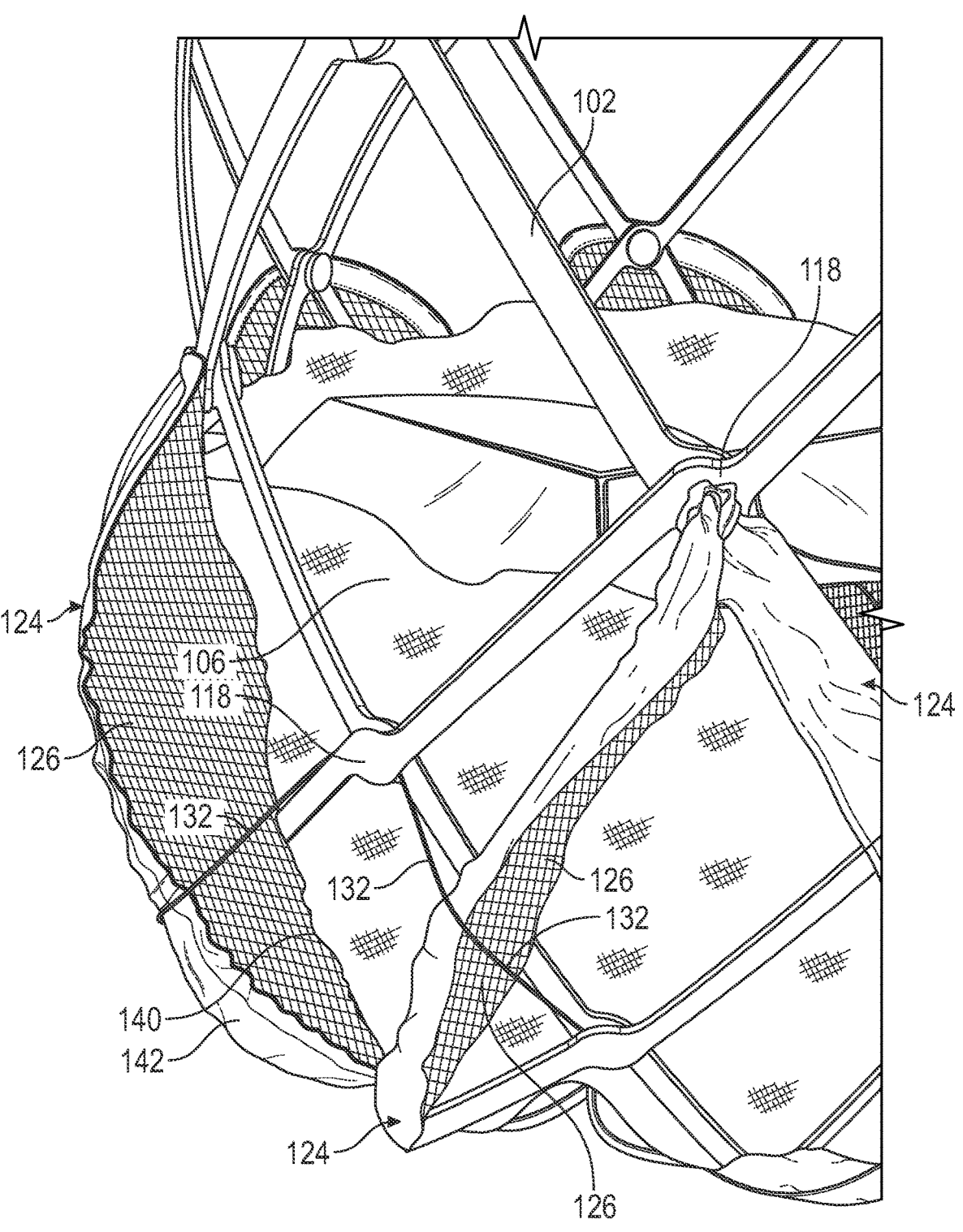
FIG. 4 depicts details of the sealing member of the prosthetic heart valve of FIG. 1.

The sealing member 108 can comprise a plurality of ribs 124 and a plurality of drapes 126, which can also be referred to as "connectors." As shown in FIG. 2, the ribs 124 are coupled to and extend radially outwardly from the frame 102. As shown in FIG. 4, the drapes 126 are coupled to and extend radially between the frame 102 and the ribs 124. In this manner, the ribs 124 act as a support structure for the drapes 126, and the drapes 126 occlude gaps between the frame 102 and the ribs 124. In some embodiments, each drape 126 can have an inner longitudinally-extending edge 140 connected to the skirt 106 and an outer longitudinally-extending edge 142 connected to a rib 124.

The ribs 124 can be coupled to the frame 102 in various ways. For example, the ribs 124 and the frame 102 can be coupled by welding, fasteners (e.g., rivets, pins, screws), sutures, adhesive, and/or other suitable means for coupling.

Referring again to FIG. 2, the ribs 124 can have first end portions 128 (the lower end portions as illustrated in FIG. 2) and second end portions 130 (the upper end portions as illustrated in FIG. 2). In some embodiments, the first end portions 128 can be coupled to the inflow end portion 110 of the frame 102, and the second end portions 130 can be coupled to the intermediate portion 114 of the frame 102. In other embodiments, the first and/or second end portions 128, 130 can be coupled to various other portions (e.g., the outflow end portion 112) of the frame 102.

In certain embodiments, the first and second end portions 128, 130 of the ribs 124 can be coupled to respective junctions 118 of the frame 102. For example, in the illustrated embodiment, the first end portions 128 are coupled to a first circumferential row of junctions (i.e., counting from the inflow end portion 110), and the second end portions 130 are coupled to a fourth circumferential row of junctions. In other embodiments, the first and/or second end portions 128, 130 can be coupled to various other rows of junctions.

In particular embodiments, the first end portion 128 of each rib 124 can be circumferentially offset relative to the respective second end portion 130 such that the ribs 124 are angled relative to the longitudinal axis of the prosthetic heart valve 100 when the prosthetic heart valve 100 is in the radially-expanded configuration. In some embodiments, the first end portions 128 of adjacent ribs 124 can be coupled to the frame 102 at or near the same location on the frame, and the second end portions 130 of adjacent ribs 124 can be coupled to the frame 102 at or near the same location on the frame. As such, the ribs 124 can, for example, form in a zig-zag or undulating pattern when the prosthetic heart valve 100 is in the radially-expanded configuration (e.g., FIG. 1).

The first and second end portions 128, 130 of the ribs 124 can be coupled to the frame 102 at locations in which the relative distance between the locations changes as the prosthetic heart valve moves between the radially-expanded/axially-foreshortened configuration and the radially-compressed/axially-elongated configuration.

The ribs 124 can be sized and configured such that the length of the ribs 124 between their opposing ends is longer than the straight-line distance between the locations at which the first and second end portions 128, 130 are attached to the frame 102 when the prosthetic heart valve 100 is in the radially-expanded configuration (e.g., FIG. 1). Accordingly, the ribs 124 can flare radially outwardly from the frame 102 in the radially-expanded configuration.

Figure 3:
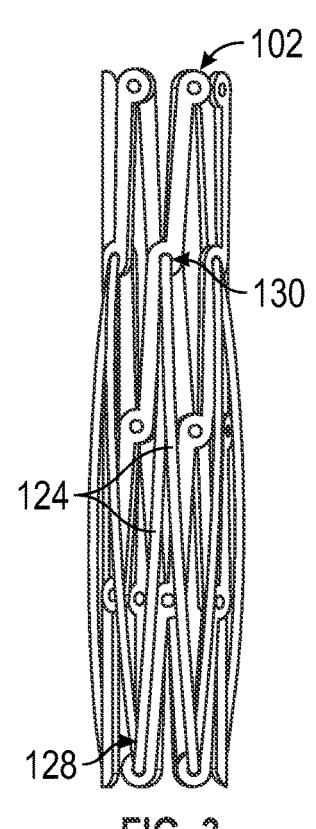
FIG. 3 depicts the frame and the sealing member (only partially shown) of the prosthetic heart valve of FIG. 1 in a radially-compressed configuration.

The ribs 124 can also be sized and configured such that the length of the ribs 124 is equal or approximately equal to the distance between the locations at which the first and second end portions 128, 130 are attached to the frame 102 when the prosthetic heart valve 100 is in the radially-compressed configuration (e.g., FIG. 3). Thus, the ribs 124 can be radially disposed against the frame 102 in the radially-compressed configuration. As shown, in particular embodiments, the ribs 124 can be configured such that the ribs 124 have an "S" shape in the radially-compressed configuration.

The length of the ribs 124 and/or the location to which the ribs 124 are attached to the frame 102 can be sized and/or configured to adjust the extent to which the ribs 124 radially expand relative to the frame 102. For example, ribs having relatively longer length can expand farther radially outwardly than ribs having relatively shorter length (assuming they are attached to the frame at the same position relative to the longitudinal axis of the prosthetic heart valve 100).

In some embodiments, the ribs 124 can be sized and/or positioned relative to the frame 102 such that each of the ribs can radially expand equidistantly from the frame 102. This can be accomplished, for example, by forming each of the ribs 124 with the same length and coupling the ribs to the frame 102 at the same position relative to the longitudinal axis of the frame. It can also be accomplished, for example, by forming one or more of the ribs 124 with a different length than at least one other rib and coupling one or more of the ribs to the frame with different spacing between the first and second end portions 128, 130 than at least one other rib.

In other embodiments, one or more of the ribs 124 can be sized and/or positioned relative to the frame 102 such that one or more of the ribs can radially expand relatively more or less than at least one other rib. This can be accomplished, for example, by forming one or more of the ribs 124 with a different length than at least one other rib and coupling one or more of the ribs to the frame with different spacing between the first and second end portions 128, 130 than at least one other rib.

The ribs 124 can be formed from a resilient material such that the ribs 124 tend not to plastically deform when ribs compress and expand as the prosthetic heart valve 100 moves between the radially-expanded configuration and the radially-compressed configuration. This can be accomplished, for example, by forming the ribs from a relative flexible material such as nitinol, stainless steel, or a suitable biocompatible polymer.

Although the drapes 126 are shown in a mesh-like pattern for purposes of illustration, the drapes can comprise a tightly woven or sheet-like material. In some embodiments, the drapes 126 can comprise a flexible fabric or material configured to occlude or restrict blood flow, including PET, polytetrafluoroethylene ("PTFE"), expanded polytetrafluoroethylene ("ePTFE"), polyurethane, and/or polyester. In certain embodiments, the drapes 126 can be formed from the same material as the skirt 106 (e.g., PET). In other embodiments, the drapes 126 and the skirt 106 can be formed from different materials. For example, the drapes 126 can be formed from PTFE and the skirt 106 can be formed from polyester, or vice versa.

The drapes 126 can be coupled to the ribs 124 and/or the skirt 106 in various ways. For example, in some embodiments, each of the drapes 126 can be wrapped around a respective rib 124 and coupled to itself (e.g., with fasteners, sutures, adhesive, ultrasonic welding, and/or other suitable means for coupling). In other embodiments, the drapes 126 can be coupled to the ribs 124 without wrapping the drapes around the ribs. The drapes 126 can be coupled to the skirt 106, for example, with fasteners, sutures, adhesive, ultrasonic welding, and/or other suitable means for coupling. In one example, the edge 140 of each drape 126 can be sutures to the skirt 106 along the entire length of the edge 140, such as with a running stitch.

The drapes 126 can be sized and/or configured such that the drapes slacken and/or fold when the prosthetic heart valve 100 is compressed from the radially-expanded configuration to the radially-compressed configuration. This allows the ribs 124 to compress radially inwardly against the frame 102, and thus reduces the radial profile of the prosthetic heart valve in the radially-compressed configuration. The drapes 126 can also be sized and/or configured such that the drapes tighten and/or unfold when the prosthetic heart valve 100 is expanded from the radially-compressed configuration to the radially-expanded configuration.

Optionally, the sealing member 108 can further comprise a plurality of retaining members or cords 132. The cords 132 can be coupled to and extend from the frame 102 to the ribs 124. The cords 132 can, for example, be configured to retain the ribs 124 at a desired spacing and/or configuration relative to the frame 102.

The cords 132 can, for example, be coupled to the frame 102 and the ribs 124 at locations between the first and second end portions 128, 130 of the ribs. For example, in some embodiments, the cords 132 can be coupled to and extend from junctions 118 of the frame 102 that are disposed between the junctions to which the first and second end portions 128, 130 of the ribs 124 are attached.

In some embodiments, each rib 124 has two cords 132 coupled thereto. In other embodiments, each rib 124 can have more or less than two cords 132 coupled thereto. In some embodiments, there can be a single cord that is coupled to (e.g., wrapped around) all of the ribs 124 and to the frame 102.

The cords 132 can be formed from a relatively flexible, inelastic material such as nylon thread or stainless-steel wire. In this manner, the cords 132 can slacken and/or fold when the prosthetic heart valve 100 is crimped from the radially-expanded configuration to the radially-compressed configuration, and the cords can tighten and/or unfold when the prosthetic heart valve is expanded from the radially-compressed configuration to the radially-expanded configuration.

The length of the cords 132 can be sized and/or configured to control the extent to which the ribs 124 can radially expand relative to the frame 102. For example, cords 132 having relatively shorter length can retain the ribs 124 radially closer to the frame 102 than cords having relatively longer length. In some embodiments, the cords 132 can be sized and/or positioned relative to the ribs 124 such that each of the ribs can radially expand equidistantly from the frame 102. In other embodiments, one or more of the cords 132 can be sized and/or positioned relative to the ribs 124 such that the one or more of the ribs can expand relatively more or less than at least one other rib.

The length of the cords 132 can also be sized and/or configured to control the radially-expanded configuration (e.g., shape) of the ribs 124. For example, in one particular embodiment, two axially-spaced cords 132 extending in opposing circumferential directions can be coupled to each rib 124 between the first and second end portions 128, 130 of the rib 124. The cords 132 can each have a length that is less than the straight-line distance between the point on the frame 102 to which the cords 132 are attached and the rib 124 when the rib is in the radially-expanded configuration. As such, the cords 132 can cause the rib 124 to have an "S" shape when the rib is in the radially-expanded configuration.

The location at which each of the cords 132 is attached to the ribs 124 can be configured to adjust the shape (e.g., arc) of the ribs 124. In some embodiments, the location at which each of the cords 132 is attached to the ribs 124 can be configured such that the shape of each of the ribs is the same when the prosthetic heart valve 100 is in the radially-expanded configuration. In other embodiments, the location at which one or more of the cords 132 is attached to the ribs 124 can be configured such that the shape of the one or more ribs is different than at least one other rib when the prosthetic heart valve 100 is in the radially-expanded configuration.

In lieu of or in addition to the cords 132, the ribs 124 can be shape-set in the desired configuration. In such embodiments, the ribs 124 can be formed from a shape-memory material such as nitinol.

The prosthetic heart valve 100 can be releasably coupled to a delivery apparatus and crimped to the radially-compressed configuration. Although not shown, the prosthetic heart valve 100 can include an actuation mechanism that is coupled to the frame 102 of the prosthetic heart valve 100 and that, in cooperation with the delivery apparatus, is configured to incrementally move the prosthetic heart valve between the radially-compressed and radially-expanded configurations. Additional details regarding the actuation mechanism and the delivery apparatus can be found, for example, in U.S. Application No. 62/430,810 and U.S. Patent Application Publication No. 2018/0153689.

In the radially-compressed configuration, the prosthetic heart valve 100 can be advanced percutaneously to a patient's heart and positioned in the annulus of a native valve. The prosthetic heart valve 100 can be expanded from the radially-compressed configuration to the radially-expanded configuration.

In the radially-expanded configuration, the sealing member 108 can engage the tissue of the native annulus adjacent the prosthetic heart valve 100 and fill in any gaps that may exist between the frame 102 of the prosthetic heart valve 100 and the native annulus. In this manner, the sealing member 108 can, for example, reduce and/or prevent blood from flowing around the prosthetic heart valve 100 between frame 102 and the native annulus.

Figure 5:
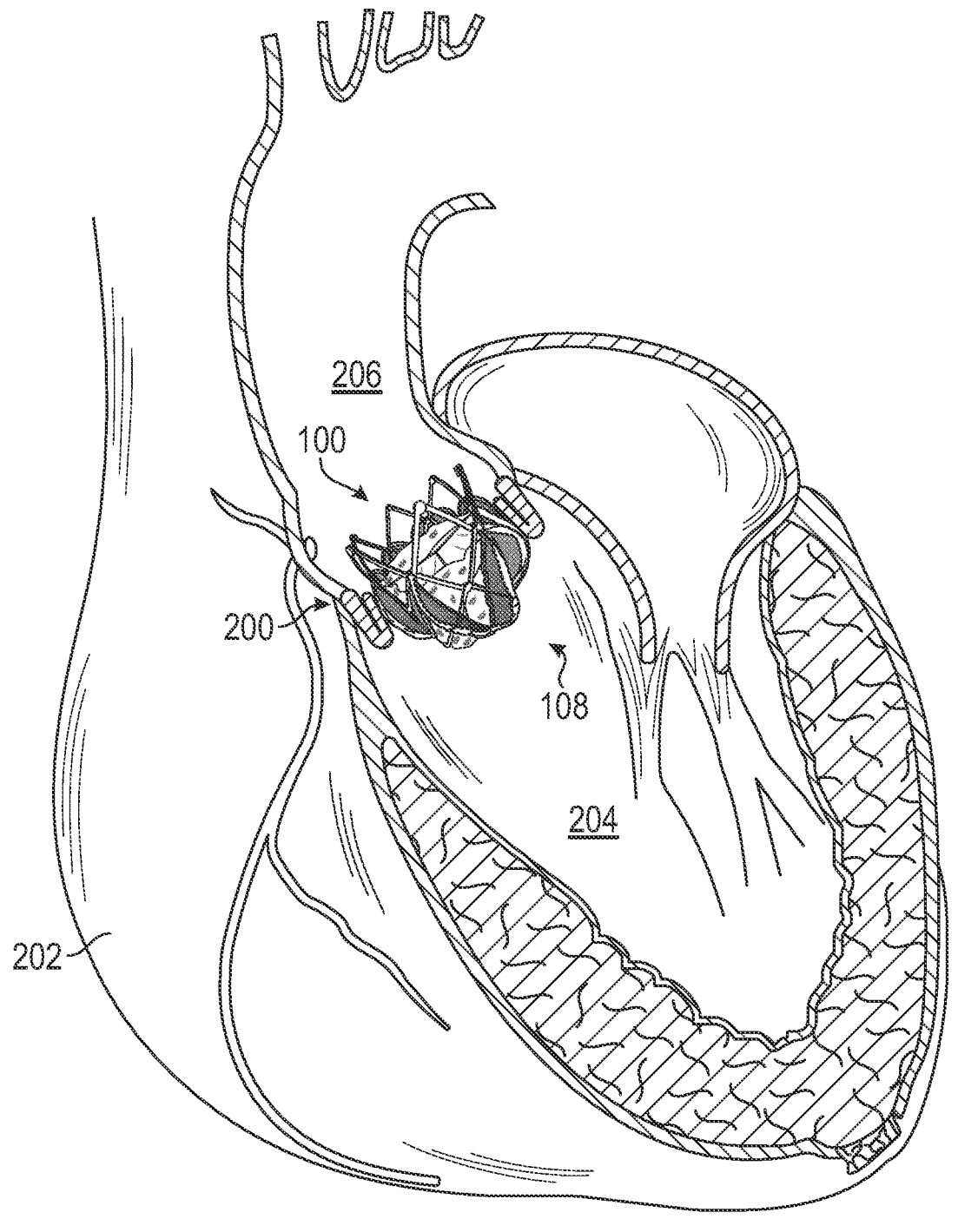
FIG. 5 depicts the prosthetic heart valve of FIG. 1 implanted in a native aortic valve of a heart (shown in partial cross-section).

For example, FIG. 5 shows the prosthetic heart valve 100 in the radially-expanded configuration and disposed within a native aortic valve 200 of a heart 202 (shown in partial cross section). As shown, the sealing member 108 can engage the tissue of the native annulus and/or leaflets adjacent the prosthetic heart valve 100 and occlude any gaps that may exist therebetween. Accordingly, the sealing member reduces and/or prevents blood from flowing around the prosthetic heart valve 100 between the left ventricle 204 and the aorta 206.

The prosthetic heart valve 100 can be secured within the native annulus and released from the delivery apparatus. After the prosthetic heart valve 100 is released, the sealing member 108 can continue to reduce and/or prevent PVL.

Figure 6:
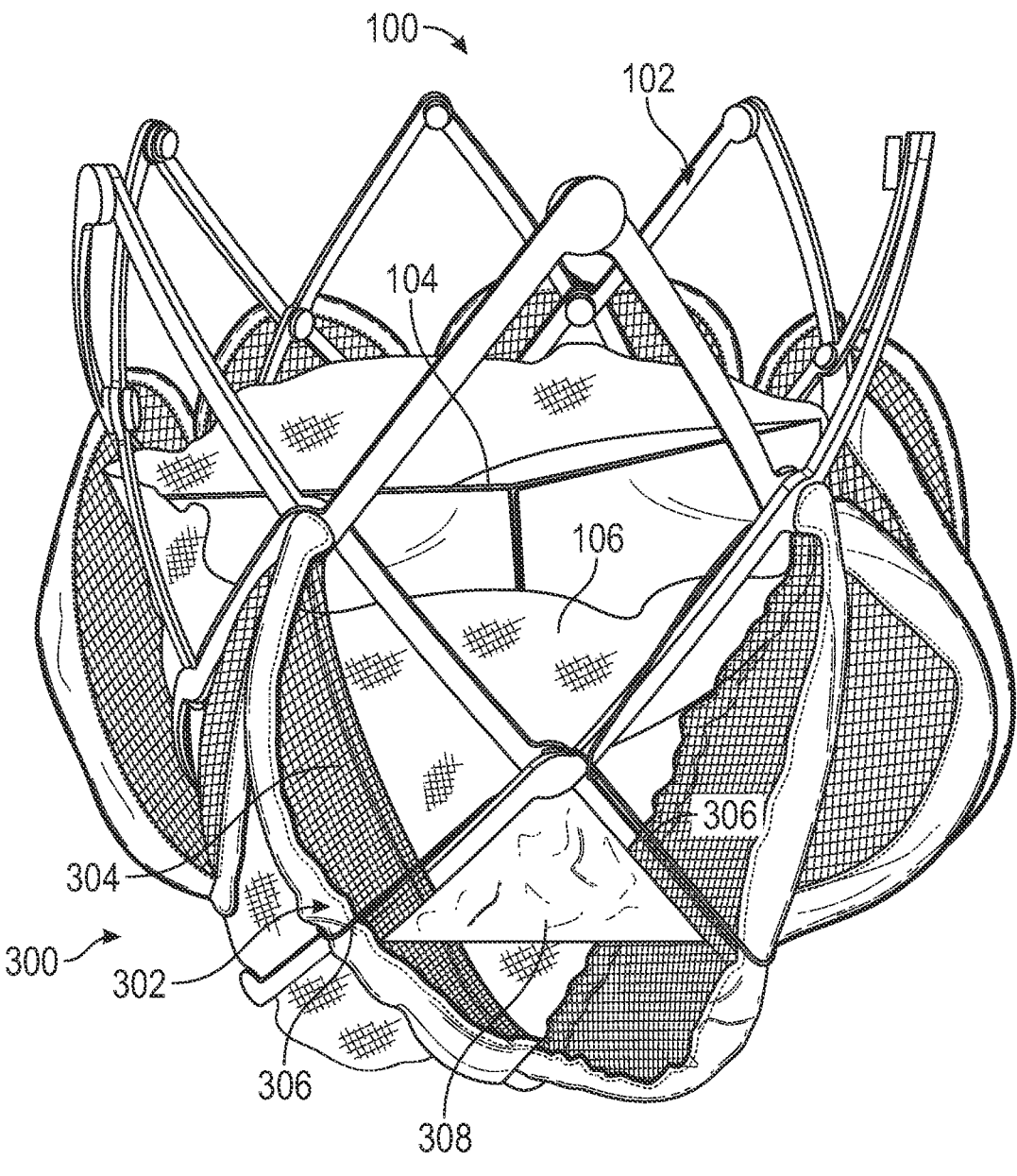
FIG. 6 depicts the prosthetic heart valve of FIG. 1 with a sealing member, according to another embodiment.

FIG. 6 shows an exemplary embodiment of a sealing member 300 coupled to the prosthetic heart valve 100 in lieu of the sealing member 108. The sealing member 300 can comprise a plurality of ribs 302 and a plurality of first drapes 304. The sealing member 300 can also optionally comprise a plurality of cords 306 and/or a plurality of second drapes 308.

The ribs 302, the first drapes 304, and the cords 306 can, for example, be configured similar to the ribs 124, the drapes 126, and the cords 132 of the prosthetic heart valve 100, respectively.

The second drapes 308 can be coupled to and extend circumferentially between adjacent pairs of the ribs 302. The second drapes 308 can also be coupled to extend radially outwardly from the skirt 106. In this manner, the second drapes 308 can, for example, provide an additional and/or alternative means for reducing and/or eliminating PVL than the first drapes 304.

In embodiments in which the sealing member 300 includes the cords 306, the second drapes 308 can extend in a plane defined by the cords 306. In other such embodiments or embodiment in which the sealing member 300 does not include the cords 306, the second drapes 308 can extend in various other planes.

In particular embodiments, the second drapes 308 can extend from the skirt 106 in planes that are at least approximately parallel to a plane perpendicular to the longitudinal axis of the prosthetic heart valve 100. In other embodiments, the second drapes 308 can extend from the skirt 106 in planes that are at angled relative to a plane perpendicular to the longitudinal axis of the prosthetic heart valve 100. For example, is some embodiments, the second drapes 308 can define a plane that is angled approximately 10-80 degrees relative to a plane perpendicular to the longitudinal axis of the prosthetic heart valve 100. In particular embodiments, the second drapes 308 can define a plane that is angled approximately 25-65 degrees or approximately 45 degrees relative to a plane perpendicular to the longitudinal axis of the prosthetic heart valve 100.

The second drapes 308 can be coupled to the ribs 302 and/or the skirt 106 in various ways. For example, the drapes 126 can be coupled to the ribs 302 and the skirt 106 with fasteners, sutures, adhesive, ultrasonic welding, and/or other suitable means for coupling.

The second drapes 308 can comprise a flexible fabric or material configured to occlude or restrict blood flow, including PET, PTFE, ePTFE, polyurethane, and/or polyester. In some embodiments, the second drapes 308 can be formed from the same material as the first drapes 304 and/or the skirt 106 (e.g., PET). In other embodiments, at least one of the first drapes 304, the second drapes 308, and the skirt 106 can be formed from different materials. For example, the second drapes 308 can be formed from PTFE and the skirt 106 can be formed from polyester, or vice versa.

Figure 7:
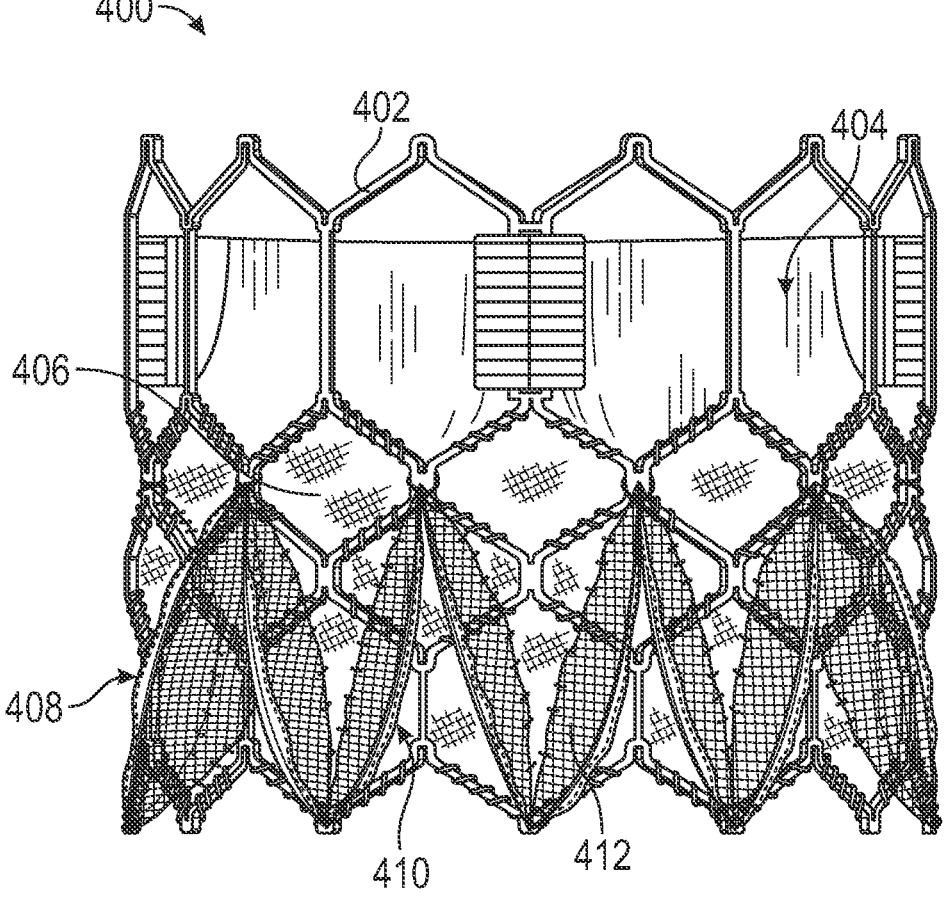
FIG. 7 depicts a prosthetic heart valve with a sealing member, according to yet another embodiment.

FIG. 7 shows an exemplary prosthetic heart valve 400. The prosthetic heart valve 400 can comprise a frame 402, a valve structure 404, a skirt 406, and a sealing member 408. The prosthetic heart valve 400 can be figured similar to the prosthetic heart valve 100, except the frame 402 of the prosthetic heart valve 400 is self-expandable and/or balloon-expandable rather than mechanically-expandable like the frame 102 of the prosthetic heart valve 100. Additional details regarding the frame 402, the valve structure 404, and the skirt 406 can be found, for example, in U.S. Pat. No. 9,974,650.

In some embodiments, the sealing member 408 can be configured similar to the sealing member 108 of the prosthetic heart valve 100. The sealing member 408 can comprise ribs 410 coupled to the frame 402 and drapes 412 extending radially outwardly between skirt 406 and the ribs 410.

In certain embodiments, the sealing member 408 can comprise cords that are coupled to and extend between the ribs 410 and the frame 402. For example, the cords can be configured similar to the cords 306 of the sealing member 300.

In particular embodiments, the drapes 412 of the sealing member 408 can be first drapes, and the sealing member can further comprise second drapes. For example, the first and second drapes of the sealing member 408 can be configured similar to the first and second drapes 304, 308 of the sealing member 300, respectively.

The features described herein regarding any example can be combined with other features described in any one or more of the other examples, unless otherwise stated. For example, the features of the sealing member 108 can be combined with the sealing member 300 and/or the sealing member 408, or vice versa. Additionally, any feature of an embodiment is independent from other components of the embodiment, unless otherwise stated.

In view of the many possible embodiments to which the principles of the disclosure may be applied, it should be recognized that the illustrated embodiments are only examples and should not be taken as limiting the scope of the claimed subject matter. Rather, the scope of the claimed subject matter is defined by the following claims and their equivalents.

The invention claimed is:

1. A prosthetic heart valve comprising:
   a frame having an inflow end portion, an outflow end portion, an intermediate portion disposed between the inflow end portion and the outflow end portion, and a plurality of struts, wherein the frame is radially collapsible and expandable between a radially-compressed configuration and a radially-expanded configuration;
   a valve component disposed within and coupled to the frame and having a plurality of leaflets; and
   a sealing member including a plurality of ribs and a plurality of connectors, wherein the plurality of ribs is coupled to and extends radially outwardly from the frame when the frame is in the radially-expanded configuration, wherein the plurality of connectors is coupled to the frame and the plurality of ribs; and
   a retaining member extending radially outwardly from the frame to the sealing member, wherein the retaining member is disposed radially outwardly from the plurality of ribs and the plurality of connectors and configured to restrict radial expansion of the plurality of ribs and the plurality of connectors.

2. The prosthetic heart valve of claim 1, wherein the plurality of connectors includes a plurality of first connectors and a plurality of second connectors, wherein the plurality of first connectors is coupled to the frame and the plurality of ribs, circumferentially aligned with the plurality of ribs, and extends radially between the frame and the plurality of ribs, and wherein the plurality of second connectors is coupled to the frame, the plurality of ribs, and the plurality of first connectors.

3. The prosthetic heart valve of claim 2, wherein each second connector of the plurality of second connectors is at least substantially perpendicular to one or more first connectors of the plurality of first connectors.

4. The prosthetic heart valve of claim 1, wherein the retaining member is a flexible cord.

5. The prosthetic heart valve of claim 1, further comprising a skirt mounted on the frame, and wherein each connector of the plurality of connectors has an inner longitudinally-extending edge sutured to the skirt and an outer longitudinally-extending edge contacting the one or more retaining members.

6. The prosthetic heart valve of claim 1, wherein the plurality of connectors comprises PET, PTFE, ePTFE, polyurethane, or polyester.

7. A prosthetic heart valve, comprising:
   a frame having an inflow end portion, an outflow end portion, an intermediate portion disposed between the inflow end portion and the outflow end portion, and a plurality of struts, wherein the frame is radially compressible and expandable between a radially-compressed configuration and a radially-expanded configuration;

a valve component disposed within and coupled to the frame and having a plurality of leaflets; and a plurality of ribs;

a plurality of connectors; and and a retaining member, wherein the plurality of ribs is coupled to and extends radially outwardly from the frame when the frame is in the radially-expanded configuration, wherein each connector of the plurality of connectors is coupled to and extends radially between the frame and a respective rib of the plurality of ribs, wherein the retaining member is coupled to the frame and the plurality of ribs so as to limit radial expansion of the plurality of ribs relative to the frame, and wherein the plurality of connectors is configured to reduce or prevent perivalvular leakage around the prosthetic heart valve.

8. The prosthetic heart valve of claim 7, further comprising a fabric skirt coupled to the plurality of struts of the frame, and wherein the plurality of connectors is sutured to the fabric skirt and extends radially outwardly therefrom.

9. The prosthetic heart valve of claim 7, wherein the retaining member is a flexible cord.

10. The prosthetic heart valve of claim 9, wherein the flexible cord is a nylon thread.

11. The prosthetic heart valve of claim 9, wherein the flexible cord is a stainless-steel wire.

12. The prosthetic heart valve of claim 9, further comprising a skirt mounted on the frame, and wherein each connector of the plurality of connectors has an inner longitudinally-extending edge sutured to the skirt and an outer longitudinally-extending edge contacting the one or more retaining members.

13. The prosthetic heart valve of claim 9, wherein the plurality of connectors comprises PET, PTFE, ePTFE, polyurethane, or polyester.

14. The prosthetic heart valve of claim 12, wherein the flexible cord is a nylon thread.

15. The prosthetic heart valve of claim 12, wherein the flexible cord is a stainless-steel wire.

* * * * *